(12) United States Patent
Grabowski et al.

(10) Patent No.: US 6,890,335 B2
(45) Date of Patent: May 10, 2005

(54) BONE FIXATION DEVICE

(75) Inventors: John J. Grabowski, Bloomington, MN (US); Kevin V. Guenther, Carver, MN (US)

(73) Assignee: Zimmer Spine, Inc., Edina, MN (US)

( * ) Notice: Subject to any disclaimer, the term of this patent is extended or adjusted under 35 U.S.C. 154(b) by 280 days.

(21) Appl. No.: 09/939,523

(22) Filed: Aug. 24, 2001

(65) Prior Publication Data

US 2003/0040749 A1 Feb. 27, 2003

(51) Int. Cl.[7] .............................................. A61B 17/58
(52) U.S. Cl. ........................................................ 606/71
(58) Field of Search ............................... 606/61, 69–73

(56) References Cited

U.S. PATENT DOCUMENTS

| | | | |
|---|---|---|---|
| 3,659,595 A | | 5/1972 | Haboush |
| 3,695,259 A | * | 10/1972 | Yost ............................ 606/69 |
| 5,549,612 A | | 8/1996 | Yapp et al. |
| 5,569,247 A | * | 10/1996 | Morrison ....................... 606/61 |
| 5,616,144 A | | 4/1997 | Yapp et al. |
| 5,797,912 A | | 8/1998 | Runciman et al. |
| 5,807,396 A | | 9/1998 | Ravch |
| 5,876,402 A | * | 3/1999 | Errico et al. .................... 606/61 |
| 5,904,683 A | | 5/1999 | Pohndorf et al. |
| 5,931,838 A | * | 8/1999 | Vito ............................ 606/61 |
| 6,193,721 B1 | | 2/2001 | Michelson |
| 6,413,259 B1 | * | 7/2002 | Lyons et al. ................... 606/69 |

FOREIGN PATENT DOCUMENTS

| | | |
|---|---|---|
| FR | 2 823 096 A1 | 10/2002 |
| WO | WO 98/34553 | 8/1998 |
| WO | WO 98/51226 | 11/1998 |
| WO | WO 99/56653 | 11/1999 |

* cited by examiner

*Primary Examiner*—Kevin Shaver
*Assistant Examiner*—Michael B. Priddy
(74) *Attorney, Agent, or Firm*—Faegre & Benson LLP

(57) ABSTRACT

A bone fixation device is provided that includes one or more plates and one or more screws having an acruate outer surface. One or more fastener-receiving apertures with a frustoconical inner surface extend through the plate. The bone fixation device may also include one or more locking arrangements that are configured to secure one or more screws in one or more fastener-receiving apertures.

45 Claims, 10 Drawing Sheets

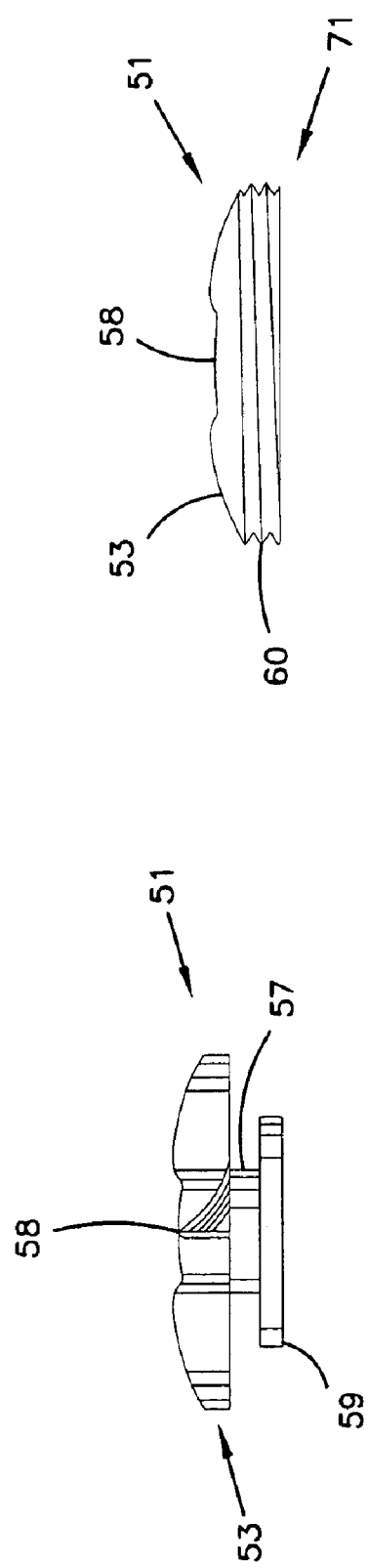

BONE FIXATION DEVICE

BACKGROUND

1. Field of the Invention

The invention relates generally to bone fixation devices, and in particular, bone fixation devices for fusion of the human cervical spine from an anterior approach.

2. Background

Cervical plating systems are used to align and maintain adjacent cervical vertebrae in a selected spatial relationship to facilitate fusion of the vertebrae. Generally, cervical plating systems include plates and screws for aligning and holding vertebrae in a desired position relative to one another. In known plating systems, there have been problems with loosening and failure of the hardware. In particular, there have been problems with the screws migrating from the plate and potentially damaging the patient's throat.

Additionally, there have been problems with "creeping substitution" in known plating systems. In "creeping substitution", bone at the interface between the graft and vertebrae is removed by natural biological processes prior to the growth of new bone. Although the plates are capable of holding the vertebrae in proper alignment, they tend to hold the vertebrae apart during resorption of the bone, thus forming gaps at the fusion site. Consequently, fusion may not occur. Such failure is known as pseudoarthrosis. When such a failure occurs, the hardware itself may break or become loosened from the spine, and may therefore require further surgical procedures to remove the broken components and to attempt fusion.

SUMMARY

The invention provides a bone fixation device that includes one or more plates and one or more fasteners. The one or more plates each have a bone-contacting surface and an upper surface opposite the bone-contacting surface. One or more fastener-receiving apertures extend through the plate from the upper surface to the bone-contacting surface. According to the invention, one or more fastener-receiving apertures have a frustoconical inner surface and one or more fasteners have a head with an arcuate outer surface. In one embodiment, the fastener is a screw. The bone fixation device may also include one or more locking arrangements that are configured to secure one or more fasteners in one or more apertures.

In one embodiment, the locking arrangement includes a bore within the upper surface of the plate, wherein the inner surface of the bore includes at least one groove. The locking arrangement also includes at least one locking element having a head configured to secure the fastener within the fastener-receiving aperture and a base having at least one projection configured to be received within the at least one groove. In another embodiment, the locking arrangement includes a bore and a locking element, wherein a deformable member is disposed between the locking element and the inner surface of the bore. If desired, the deformable member can be used in connection with a threaded bore and locking element to provide a locking arrangement with a predetermined initial and final position.

BRIEF DESCRIPTION OF THE DRAWINGS

FIG. 16 is a side elevational view of an alternative embodiment of a locking element.

FIG. 17 is a side elevational view of an alternative embodiment of a locking element.

DETAILED DESCRIPTION

The invention provides a bone fixation device that includes one or more plates and one or more fasteners. Although the invention is described with respect to a bone fixation device for fusing vertebrae, it is not so limited. The device may be used in the fixation of a wide variety of bones. If desired, the plate can be used in combination with spinal fusion implants, such as those described in U.S. Pat. No. 5,458,638, the disclosures of which is incorporated herein in its entirety.

1. Plates

Figure 1:
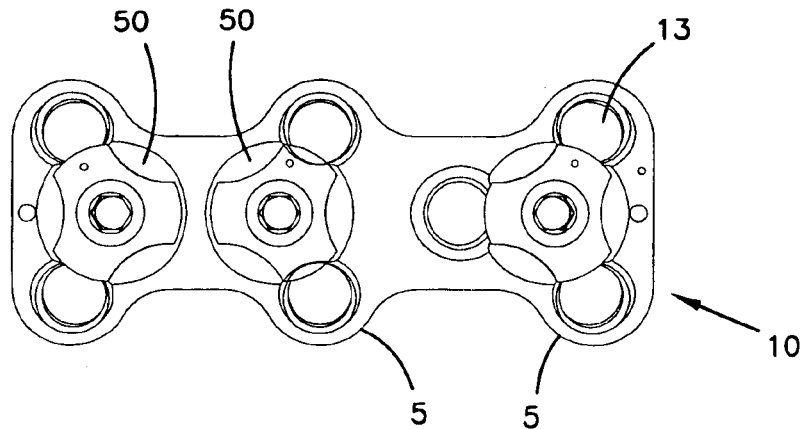
FIG. 1 is a top plan view of a plate of one embodiment of the bone fixation device of the invention.
Figure 2:
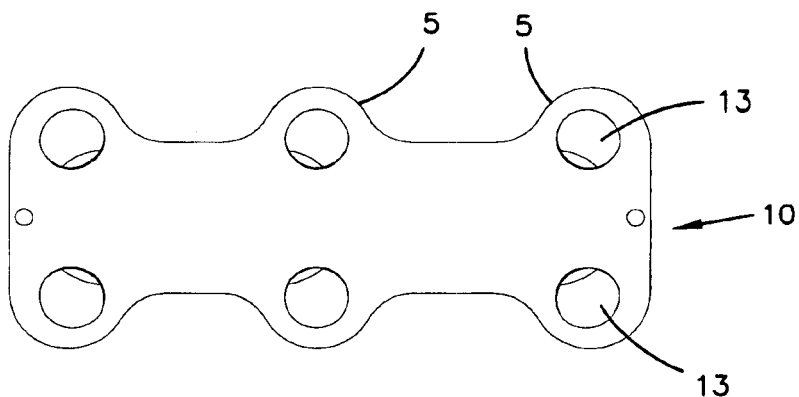
FIG. 2 is a bottom plan view of a plate of one embodiment of the bone fixation device of the invention.

Referring now to FIG. 1, the bone fixation device includes one or more plates 10. Although the plate 10 shown in FIG.

1 is designed as an anterior cervical plate (i.e., for use in a two level fusion for fusing three adjacent cervical vertebrae), the plate 10 can be used to fuse other bones, including other vertebrae (e.g., thoracic or lumbar) or other structural bones, such as long bones (e.g., femur or humerus).

The plates 10 each have a bone-contacting surface 11 and an upper surface 12 opposite the bone-contacting surface (See FIGS. 3–7). One or more fastener-receiving apertures 13 extend through the plate from the upper surface 12 to the bone-contacting surface 11. In one embodiment, the apertures 13 are configured to receive bone screws (See e.g., FIGS. 10 and 11). However, in alternative embodiments the plate may be secured to a bone via a fastener such a nail, spike, tack, staple, wire, rivet, hook, clamp, molley/anchor, expandable fastener, bolt, etc . . . If desired, the fastener-receiving apertures 13 can include lobes or lateral projections 5, typically at the corners and the center of the sides of plate 10. Generally, the lobes 5 have a rounded outline. Whether or not the fastener-receiving apertures 13 are located within lobes 5, the apertures 13 are generally located at the corners of the plates in paired sets.

Figure 8:
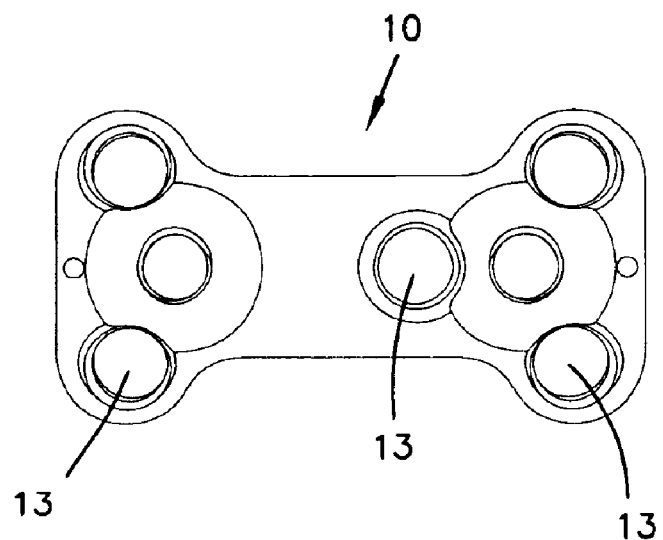
FIG. 8 is a top plan view of a plate of another embodiment of the bone fixation device of the invention.
Figure 9:
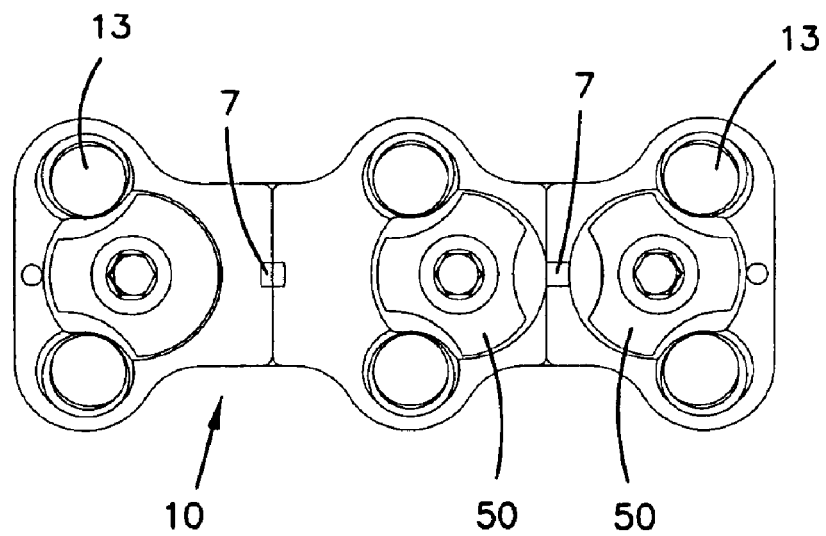
FIG. 9 is a top plan view of a plate of another embodiment of the bone fixation device of the invention.

In one embodiment, the plate 10 has a generally elongated form. For example, the outline of the plate 10 can be generally rectangular or oval in shape. The elongate form is generally suitable for use in fusing three or more adjacent vertebrae, or adjacent segments of long bones or other adjacent structural bones. In another embodiment, the plate 10 has a more truncated form (FIG. 8). The more truncated form may be suitable for fusing two vertebrae. In yet another embodiment, one or more plates 10 can be linked together to form a single device (FIG. 9). In one embodiment, the plates 10 are linked together in a rigid or fixed configuration, for example, using one or more locking tabs 7. As used herein the term "rigid or fixed" configuration refers to a configuration in which one or more plates 10 are not moveable with respect to one another once they are "locked" together. In another embodiment, the plates 10 are linked together in a dynamic configuration. As used herein, the term "dynamic" configuration refers to a configuration in which one or more plates are moveable with respect to one another when linked (i.e., rotatable with respect to one another around the longitudinal axis A—A of the plate and pivotable with respect to one another about a transverse axis a—a of the plate). It is contemplated that other shapes for the plate 10 also may be employed.

According to the invention, one or more of the fastener-receiving apertures 13 have an inner surface 14 that is at least in part frustoconical. As used herein, the term "frustoconical" refers to a surface generated by a line that passes through a vertex at a first end and traces a closed curve at a second end. Generally, the surface is bound by two planes that intersect the surface. Although the planes are frequently parallel, they need not be. The planes can be oblique or even converging. Typically, the closed curve that defines the second end is a circle, but other shapes, including but not limited to, ovals or ellipses also are suitable. Generally, the frustoconical inner surface has a minor aperture 16, proximate the vertex and a major aperture 15, proximate the closed curve. Generally, the diameter (D) of the major aperture 15 is greater than the diameter (d) of the minor aperture 16.

Figure 5:
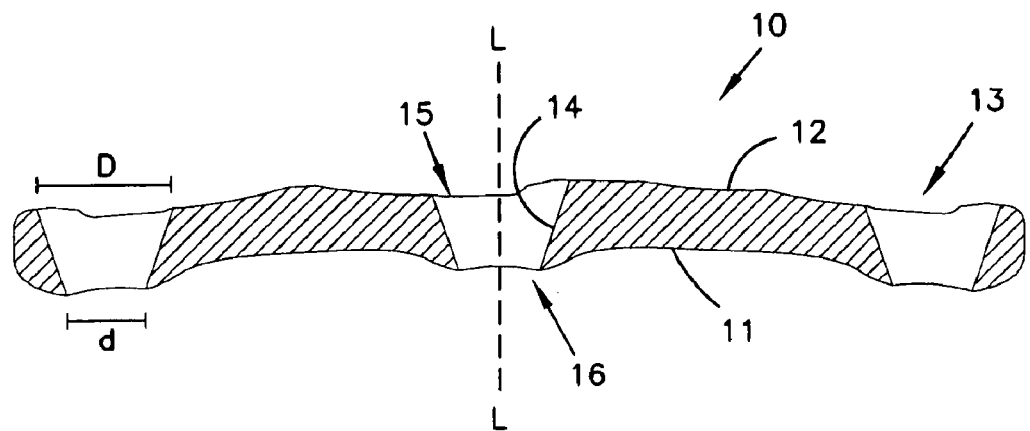
FIG. 5 is a cross sectional side elevational view of one embodiment of a plate with apertures having a frustoconical inner surface.
Figure 6:
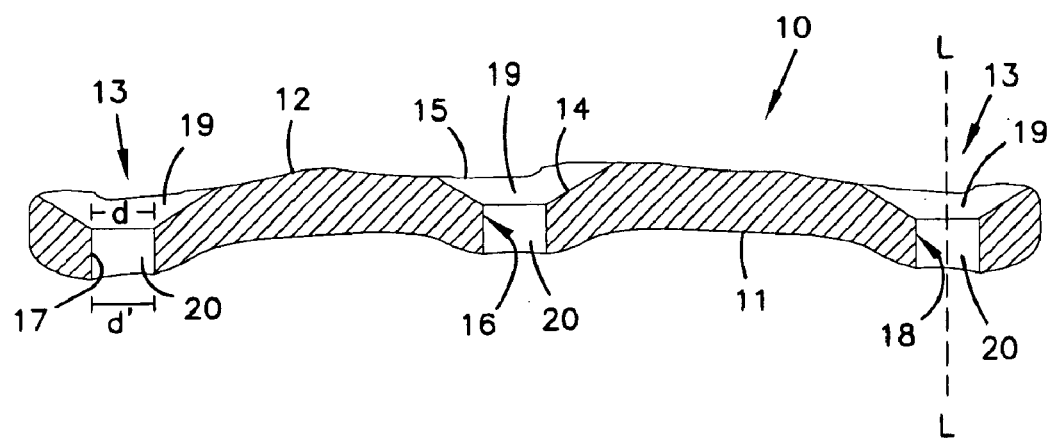
FIG. 6 is a cross sectional side elevational view of an alternative embodiment of a plate with apertures having a frustoconical inner surface.
Figure 7:
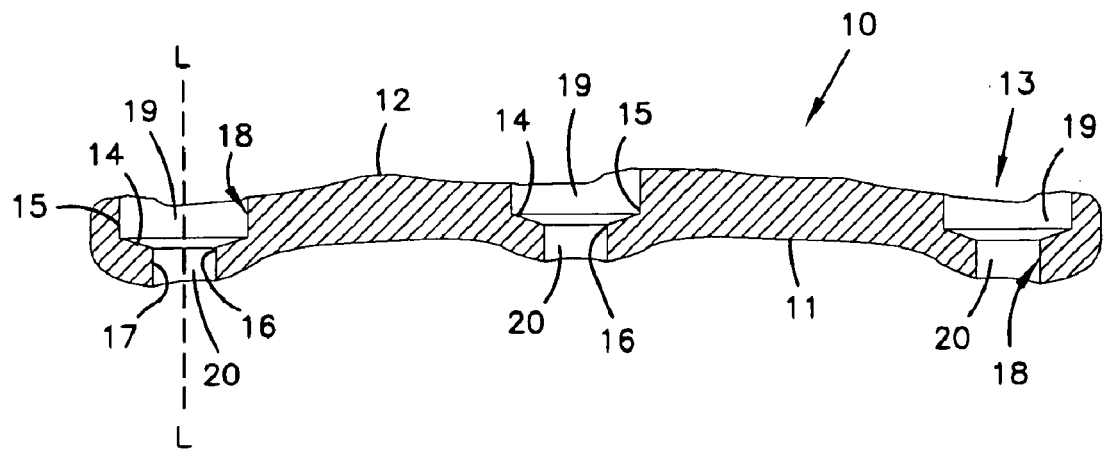
FIG. 7 is a cross sectional side elevational view of another embodiment of a plate with apertures having a frustoconical inner surface.

In one embodiment, shown in FIG. 5, the frustoconical inner surface 14 extends from the upper surface 12 of the plate 10 to the bone-contacting surface 11, such that the upper surface 12 of the plate 10 defines the major aperture 15 of the frustoconical inner surface 14 and the bone-contacting surface 11 of the plate 10 defines the minor aperture 16 of the frustoconical inner surface 14. In an alternative embodiment, the frustoconical inner surface 14 is located between the upper surface 12 and the bone-contacting surface 11, but does not intersect one or the other, or both. For example, the major aperture 15 of the frustoconcial inner surface 14 can be defined by the upper surface 12 of the plate 10, but the minor aperture 16 may be disposed at a location between the upper surface 12 and the bone-contacting surface 11 (FIG. 6). In this embodiment, the frustoconical inner surface 14 is oriented such that the minor aperture 16 is proximate the bone-contacting surface 11 and the major aperture 15 is proximate the upper surface 12 of the plate 10. Typically, in this embodiment, a channel 17 extends from the minor aperture 16 of the frustoconical inner surface 14 to the bone-contacting surface 11 of the plate 10. In this embodiment, the opening having the frustoconical inner surface 14 can be referred to as a "major opening" 19. The channel 17 extending from the major opening to the bone-contacting surface 11 can be referred to as the "minor opening" 20. Typically, the minor opening has a cylindrical inner surface 18 with a diameter (d') substantially the same as (i.e., within about 2% to about 10%) the diameter (d) of the minor aperture 16 of the frustoconical inner surface 14. In yet another embodiment, the frustoconical inner surface 14 may not intersect either the upper surface 12 or the bone-contacting surface 11 of the plate (FIG. 7). For example, the aperture 13 extending between the upper surface 12 and the bone-contacting surface 11 may include three or more segments: a top segment 18 extending from the upper surface 11; a middle segment having a frustoconical inner surface 14; and a bottom segment 17 extending from the minor aperture 16 of the frustoconical inner surface 14 to the bone-contacting surface 11 of the plate 12. The inner surface of the top segment 18, extending from the upper surface 12 of the plate toward the middle segment can be any suitable shape, including but not limited to, cylindrical, frustoconical, and parabolic. Generally, in the embodiments shown in FIGS. 6 and 7, the opening having the frustoconical inner surface 14 can be referred to as a "major opening" 19 and the opening proximate the bone-contacting surface having a diameter (d') less than or equal to the diameter (d) of the minor aperture 16 can be referred to as a "minor opening" 20. Typically, the major aperture 15 has a diameter between about 20% to about 80% greater than the diameter of the minor aperture 16, more typically, the major aperture 15 has a diameter between about 30% to about 70% greater than the diameter of the minor aperture 16, most typically the major aperture 15 has a diameter between about 40% to about 60% greater than the diameter of the minor aperture 16.

As noted above, generally, the plate 10 has one or more pairs of fastener-receiving apertures 13. When the device is used to stabilize vertebrae, the number of pairs of fastener-receiving apertures 13 generally corresponds to the number of vertebrae to be fused. For example, for a two level (three vertebrae) fusion, the plate 10 typically has three pairs of fastener-receiving apertures 13 (FIG. 1). Fastener-receiving apertures 13 may be eliminated for a single level (two vertebrae) fusion (FIG. 8), or additional fastener-receiving apertures 13 may be added if additional levels are to be fused (not shown). In one embodiment, the plate 10 is configured as an anterior cervical plate suitable for stabilizing between 2 to 5 vertebral bodies. Generally, the length of the plate will vary depending on the desired end use. For example, a lumbar or thoracic plate may be longer than a cervical plate. Typically a cervical plate has a length between about 10 mm to about 250 mm, more typically between about 15 mm to about 150 mm, most typically between about 20 mm to about 100 mm.

Figure 3:
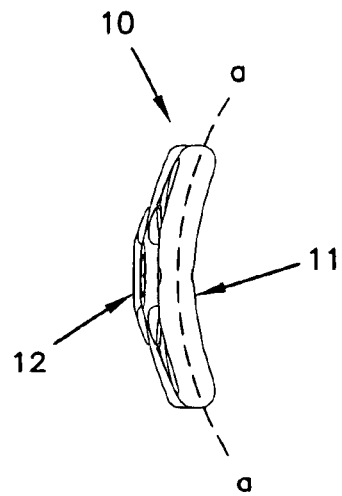
FIG. 3 is an end elevational view of a plate of one embodiment of the bone fixation device of the invention.
Figure 4:
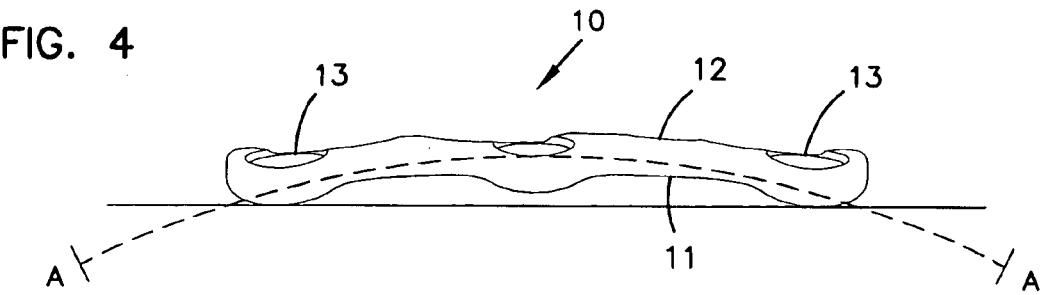
FIG. 4 is a side elevational view of a plate of one embodiment of the bone fixation device of the invention.

As shown in FIGS. 3 and 4, the plate 10 may be shaped so that the bone-contacting surface 11 has a bi-concave curvature, concave both in the longitudinal plane (A—A) (corresponding to a length of the plate 10) and in the transverse plane (a—a) (corresponding to a width of the plate 10). This embodiment is particularly advantageous when the bone fixation device is used to stabilize a vertebral column. The concave curvature in the longitudinal plane generally conforms to the shape of the anterior aspect of the vertebral column, allowing for the appropriate lordotic curvature. The concave curvature in the transverse plane can increase the contact area between the plate and the vertebrae and improve stability of the plate by reducing rocking of the plate 10 relative to the vertebral bodies, thereby reducing stress on the implant, the vertebral bodies, and surrounding tissue.

The plate 10 can be constructed from any suitable material. Preferably, the plate 10 is constructed from a biocompatible material such as stainless steel or titanium, titanium alloy, polymers and/or resorbable materials.

If desired, the bone-contacting surface 11 can have a porous, roughened, and/or textured surface and/or may be coated or impregnated with fusion promoting substances (such as bone morphogenetic proteins). The textured surface 11 can help retain the fusion promoting substances. Methods for producing textured surfaces are known, and include but are not limited to, rough blasting, etching, plasma spraying, sintering, stamping, coining, and casting. Suitable fusion promoting substances include, but are not limited to, bone morphogenetic proteins, hydroxyapatite, or hydroxyapatite tricalcium phosphate. Additionally, the plate 10 may include at least in part a resorbable material which can be impregnated with the bone growth material, so that the bone growth material is released as the plate 10 is resorbed by the body.

2. Fasteners

The bone fixation device also includes one or more fasteners 30 having an arcuate head. A variety of fasteners 30 are suitable and include, but are not limited to, spikes, wires, rivets, hooks, clamps, molley/anchors, expandable fasteners, nails, tacks, staples, etc. In one embodiment, the fastener is a screw 30 with an arcuate head. Although the description below focuses on the use of screws as fasteners, the concepts are intended apply to other fasteners as well.

Figure 10:
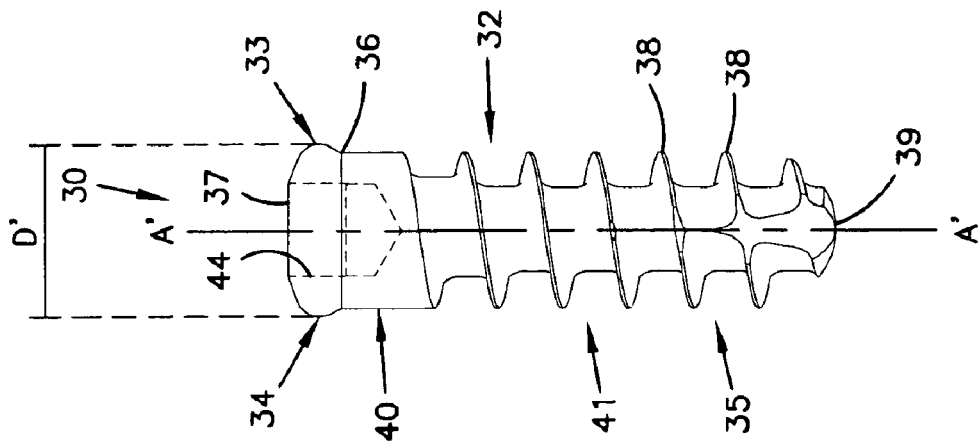
FIG. 10 is a side elevational view of a variable screw.
Figure 11A:
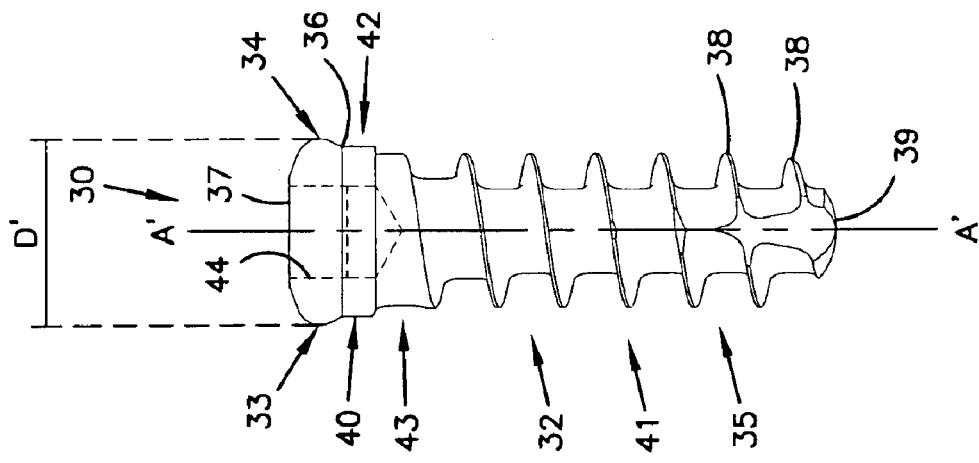
FIG. 11A is a side elevational view of a fixed screw.
Figure 11B:
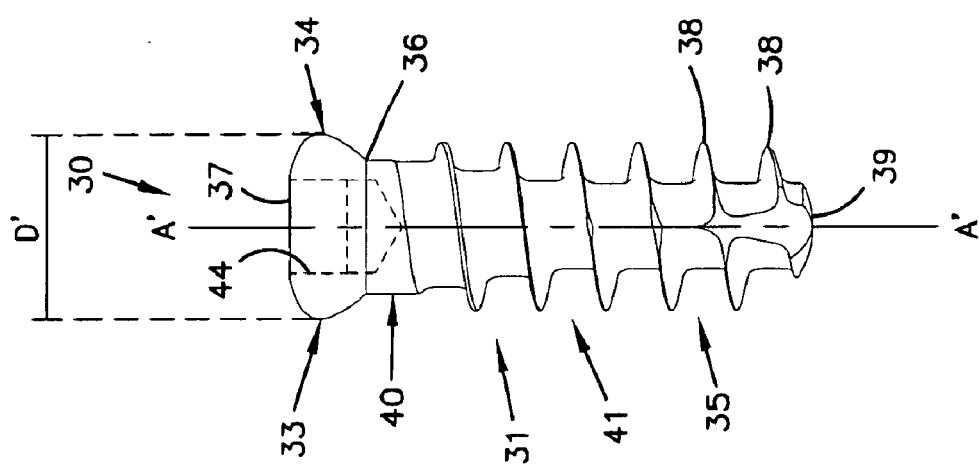
FIG. 11B is a side elevational view of a fixed screw.

FIGS. 10 and 11 (A and B) provide side elevational views of variable 31 and fixed 32 screws, respectively, suitable for use in the present invention. Generally, the screw 30 includes a screw head 33 with an arcuate outer surface 34 that extends between an upper surface 37 of the screw head 33 and a lower surface 36 of the screw head 33. The arcuate outer surface 34 in these illustrative embodiments are bulbous in shape, being not only curved about the longitudinal axis of the screw 31 or 32, but also has a curved profile when viewed from a direction generally perpendicular to the longitudinal direction, as illustrated in FIGS. 10, 11A and 11B. Generally, each screw 30 has a driver engagement member, for example, a recess 44 configured to receive the driver. Alternatively, the driver engagement member can include a projection that extends from the upper surface 37 of the screw head, wherein the projection is configured to mate with an opening in the driver.

As used herein, the term "arcuate outer surface" refers to a curved surface having a radial arc. The radius of curvature may vary, depending on the end use of the plate. For example, when used as a cervical plate, the longitudinal axis A—A may have a curvature that generally corresponds to an arc along the circumference of a circle having a radius between about 15 cm and about 30 cm, more typically between about 20 cm and about 25 cm. The transverse axis a—a may have a curvature that generally corresponds to an arc along the circumference of a circle having a radius between about 15 mm and about 25 mm, more typically between about 19 mm and about 21 mm.

The screw also includes a shaft 35 that extends from the lower surface 36 of the screw head 34. In some embodiments, the shaft 35 has more than one segment, for example, the shaft 35 may include an upper shaft 40 and a lower shaft 41. Typically, at least the lower shaft 41 is threaded with a helical thread 38 to enhance engagement between the screw 30 and the bone to which it is secured. If desired, the upper shaft 40 can be threaded, in whole or in part. Additionally, the tip 39 of the shaft 35 may be fluted by at least one cut out section so as to make the screw self-tapping.

In some embodiments, it may be desirable to taper the diameter of the shaft 35 of the screw 30. Generally, the diameter of the shaft 35 increases from the tip 39 of the screw 30 toward upper shaft 40 near the screw head 33. In one embodiment, the rate of increase in diameter is may be greater near the screw head 33. The tapered shape is designed to reduce stress risers and increase strength at the screw-plate junction.

Generally, the arcuate lower surface 36 of the screw head 33 is positioned adjacent the frustoconical inner surface 14 of the fastener-receiving aperture 13 during fixation of a bone with the device. If desired, the arcuate lower surface 36 of the screw head 33 can contact the frustoconcial inner surface 14 of the fastener-receiving aperture 13 during fixation of a bone with the device. The interface between the arcuate outer surface 34 and the frustoconical inner surface 14 is generally a ring of contact.

While not wanting to be limited by theory, it is believed that the frustoconical surface improves the contact between the plate 10 and the arcuate fastener head. In contrast to known plates that have a spherical aperture and a spherical fastener head, which may only have two points of contact between the aperture and the fastener head, combining a frustoconical surface with a fastener having an arcuate outer surface results in a ring of contact between the fastener head and the surface, thus improving stability and reducing breakage.

Generally, screw head 33 has a diameter (D') that is less than the diameter (D) of the major aperture 15 of the frustoconical inner surface 14 of the fastener-receiving aperture 13, but greater than the diameter (d) of the minor aperture 16. The diameter (D') of the screw head 33 prevents the screw 30 from being advanced completely through fastener-receiving apertures 13 of the plate 10.

The screws 30 can be constructed from any suitable material. Preferably, the screw 30 is constructed from a biocompatible material such as stainless steel, or titanium, titanium alloy, polymers and/or resorbable materials.

As discussed above, the bone-contacting surface 11 of the plate 10 is bi-concave. If one or more screws 30 are secured perpendicular to the radius of curvature A—A of the plate 10, the longitudinal axis A'—A' of the screws 30 are generally convergent and eventually "meet" at the center of the radius. Alternatively, it may be desirable to secure one or more screws 30 at an angle with respect to the radius of curvature A—A of the plate 10. The bone fixation device of the invention includes fixed and/or variable screws to allow the surgeon to optimize the screw position.

A. Fixed Screw

In some cases it may be desirable to use a fixed screw 32 in connection with the bone fixation device. Two embodiments of fixed screws are shown in FIGS. 11A and 11B. Other embodiments also are envisioned. Generally, a fixed screw 32 has little to no angular motion once it is secured within the fastener-receiving aperture 13. Typically, the fixed screw 32 is used in combination with a plate 10 that has a major opening 19 with a frustoconical inner surface 14 and a minor opening 20 proximate the bone-contacting surface 11 of the plate 10.

Generally, the fixed screw 32 has an upper shaft 40 that has a diameter that matches the diameter (d) of the minor opening 20. As used herein, the term "matches" means that the upper shaft 40 is receivable within the minor opening 20, but the diameter of the upper shaft 40 is no more than about 10% less than the diameter (d) of the minor opening 20, typically no more than about 5% less, most typically no more than about 2% less. In one embodiment, the upper shaft 40 of the fixed screw 32 includes a major component 42 proximate the lower surface 36 of the screw head 33 and a minor component 43 proximate the lower shaft. In this embodiment, the major component 42 has a diameter that matches the diameter of the minor opening 20 of the fastener-receiving aperture 13 and the minor component 43 has a diameter that is less than (i.e., at least about 20% less, more typically at least about 10% less, most typically at least about 5% less) the diameter of the minor opening 20.

B. Variable Screw

In some cases it may be desirable to use a variable screw 31 in connection with the bone fixation device. One embodiment of a variable screw is shown in FIG. 10. Other embodiments also are envisioned. The variable screw 31 can be used in connection with a plate 10 that has fastener-receiving apertures 13 with or without major 19 and minor 20 openings. Generally, a variable screw 31 has an upper shaft 40 with a smaller diameter than that of a fixed screw 32 (i.e., when designed for use with the same plate), such that the screw 31 can be positioned at an angle relative to the longitudinal axis L—L of the fastener-receiving aperture 13. When a variable screw 31 is used in connection with the plate 10 of the invention, the plate 10 can self-adjust (e.g., rotate down) as the bone that is being stabilized undergoes creeping substitution or other settling, such that the load on the device is shared between the screws, the plate and the vertebrae. Alternatively, the surgeon may want to angle one or more screws 31 at the time of implantation for other reasons. For example, when stabilizing cervical vertebrae, it may be desirable to angle the top-most screw to reduce the likelihood that the screw will enter the disc space.

Generally, the variable screw 31 includes a screw head 33 having an arcuate outer surface 34 with a diameter that is greater than the diameter of the minor opening 20 and an upper shaft 40 with a diameter that is less than the diameter of the minor opening 20. Generally, the upper shaft 40 of the variable screw has a diameter that is between about 10% and about 50% less than the diameter of the minor opening 20, more typically between about 20% and about 40% less, most typically between about 25% and about 35% less.

3. Locking Arrangements

In one embodiment, the bone fixation device includes one or more locking arrangements 50. See, for example, FIG. 1. In some embodiments, the plate 10 includes one locking arrangement 50 for each fastener 30 (a "single-lock" arrangement). In other embodiments, the plate 10 includes one locking arrangement 50 for multiple fasteners (a "multi-lock" arrangement). For example, the plate 10 may include one locking arrangement for each pair of fastener-receiving apertures 13. Thus, a plate 10 for a one level fusion (two pairs of fastener-receiving apertures 13) might have two locking arrangement 50 (FIG. 8), while plates for fusing more than two levels (three vertebrae) could have additional locking arrangements 50 corresponding to additional paired bone screw holes (FIG. 1).

Figure 12:
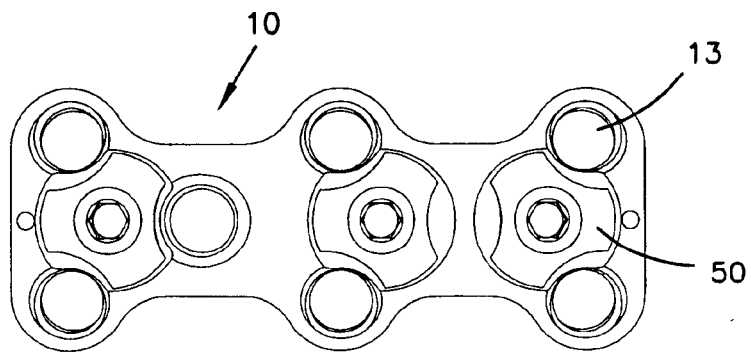
FIG. 12 is a top plan view of a plate with multi-lock locking arrangements.
Figure 13:
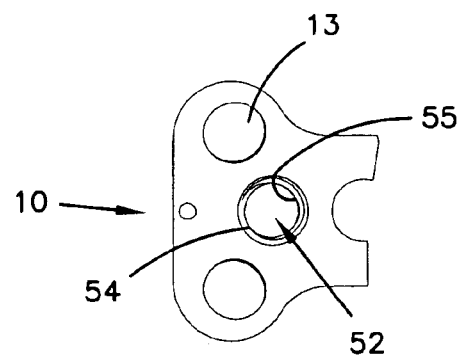
FIG. 13 is an enlarged view of a locking aperture.
Figure 20:
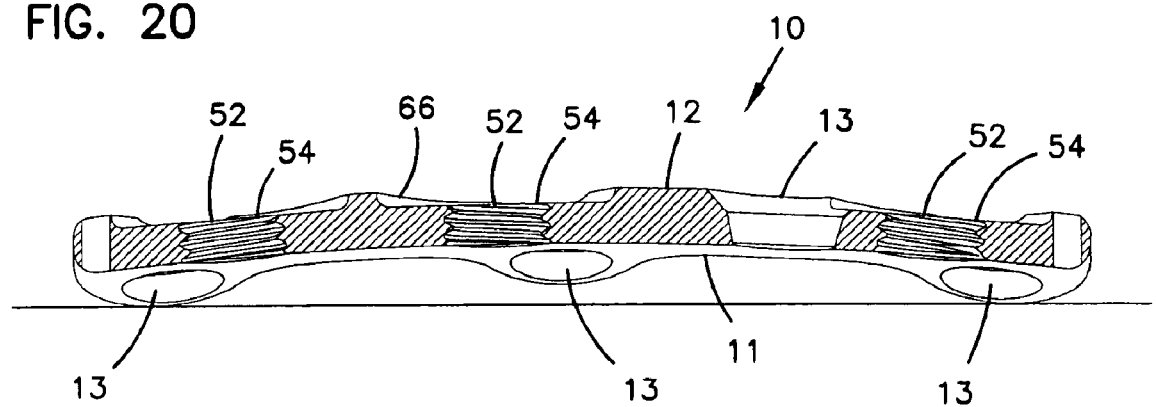
FIG. 20 is a longitudinal cross sectional view of a plate with threaded locking apertures.
Figure 21:
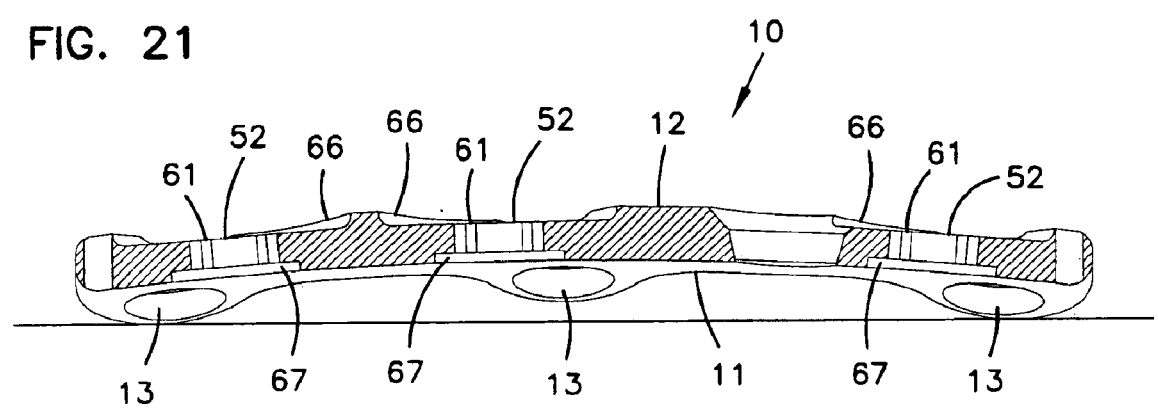
FIG. 21 is a longitudinal cross sectional view of a plate with a grooved locking aperture.
Figure 22:
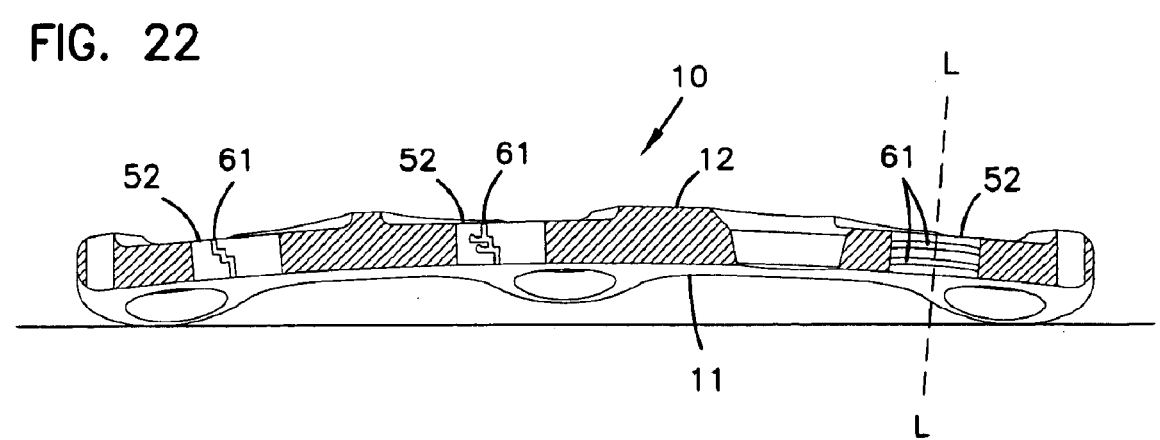
FIG. 22 is a longitudinal cross sectional view of a plate with an alternative embodiment of a grooved locking aperture.

FIG. 12 is a top plan view of a plate 10 with multi-lock locking arrangements 50 for each pair of fastener-receiving apertures 13. Many suitable locking arrangements 50 are possible. Generally, the locking arrangement 50 includes a locking element 51 (FIGS. 14–18) housed in a locking aperture 52 (FIG. 13) in the upper surface 12 of the plate 10. In one embodiment, the locking aperture 52 extends from the upper surface 12 of the plate 10 to the bone-contacting surface 11. In another embodiment, the locking aperture 51 extends from the upper surface 12 and terminates at a location between the upper surface 12 and the bone-contacting surface 11 of the plate. In yet another embodiment, the locking aperture 52 includes a first countersink 66 in the upper surface 12 of the plate 10 (FIGS. 20 & 21). In this embodiment, the locking cover 53 of the locking element 51 is typically configured to be received within the first countersink 66. In other embodiments, the locking element 51 is not recessed within the locking aperture 52 (i.e., the locking element may have a raised profile with respect to the upper surface 12 of the plate 10).

The locking element 51 can be removable or non-removable, and may or may not have a locked and unlocked position. In one embodiment, the locking element 51 is a rotable element such as a rotatable cam that has an unlocked position that permits insertion of a fastener 30 into the fastener-receiving aperture 13 and a locked position in which a locking cover 53 blocks the fastener from "backing out" of the fastener-receiving aperture 13. Alternatively, the locking element 51 is a removable element, such as a screw, which can be positioned within the locking aperture 52 after placement of the screws 30 in the fastener-receiving apertures 13. In this embodiment, the locking cover 53 may or may not be cammed. In yet another embodiment, the locking element 51 engages the locking aperture 52 via a press fit or friction fit.

Figure 14:
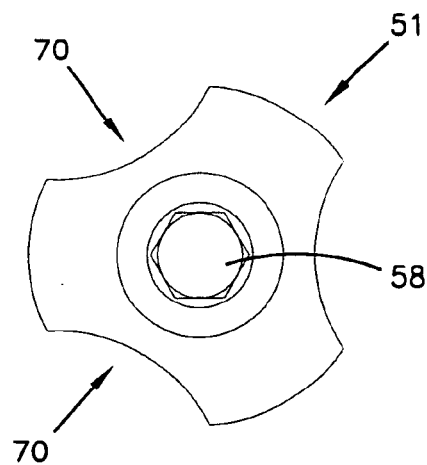
FIG. 14 is a top plan view of a locking element.
Figure 15:
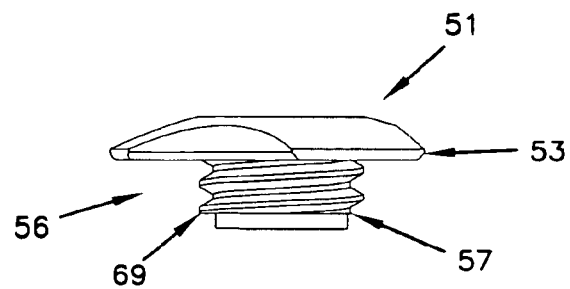
FIG. 15 is a side elevational view of a locking element.

As used herein, the term "cammed" refers to a locking element 51 having a locking cover 53 that includes one or more cutout portions 70 configured to allow the fastener 30 to pass the locking cover 53 and rest within the major opening 19 (FIG. 14). Typically, the locking cover 53 of the locking element 51 includes a driver engagement member, such as a noncircular recess 58, which is configured to engage an appropriate driver tool.

In one embodiment, the locking element 51 is constructed as a removable screw having a locking cover 53 and a threaded shaft 57 (FIG. 15), wherein the threaded shaft 57 is configured to mate with an inner surface 54 (FIGS. 13 and 20) of the locking aperture 52 that includes threads 55.

In an alternative embodiment, the locking element 51 is constructed as a rivet (FIG. 16) that includes a locking cover 53, a shaft 57, and a flange 59. The rivet is configured to mount to the locking aperture 52. The rivet can be a separate, removable component from the plate, or it can be non-removable, formed as part of the plate 10 during the manufacturing process.

The locking element 51 can be a "cap" 71 that is merely a locking cover 53 (FIG. 17) with a threaded exterior surface 60, wherein the threads on the locking cover 53 are configured to mate with an inner surface 54 of the locking aperture 52, which includes one or more threads 55 (typically helically wound threads).

A. Projection/Groove Locking Arrangement

Figure 18:
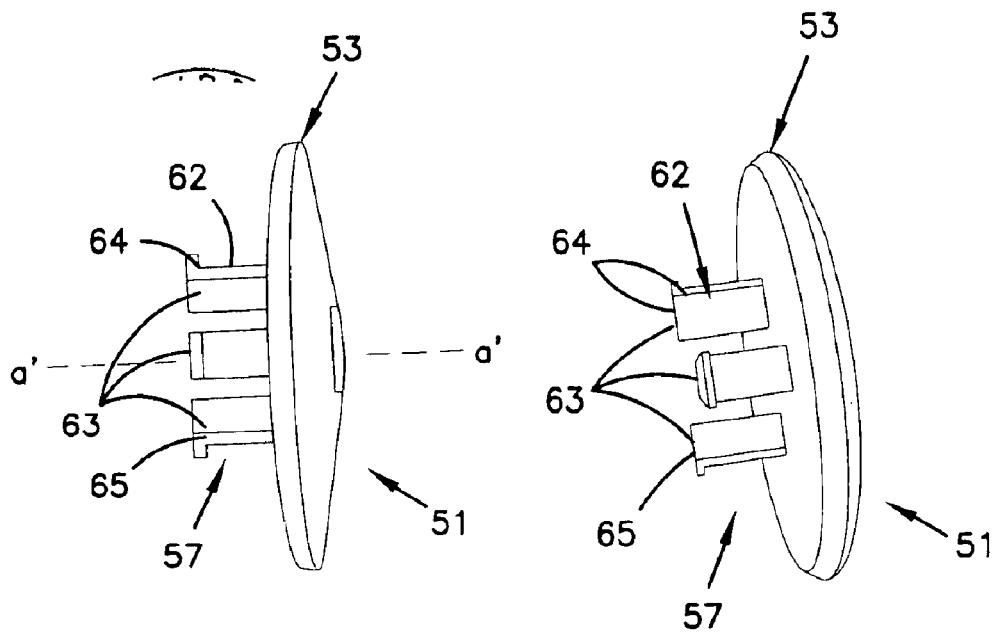
FIG. 18 is a side elevational view of an alternative embodiment of a locking element.

In one embodiment, the locking arrangement 50 includes at least one locking aperture 52 within the upper surface 12 of the plate 10, wherein the locking aperture 52 has an inner surface 54 including at least one groove 61 (FIGS. 19 to 25). The locking arrangement 50 also includes at least one locking element 51 that includes a locking cover 53 configured to secure the fastener 30 within the fastener-receiving aperture 13 and a shaft 57 that includes at least one projection 62 configured to be received within the at least one groove 61 (FIG. 18). To secure the locking element 51 within the locking aperture 52, at least one projection 62 of the locking element 51 is aligned with at least one groove of the locking aperture 52. Generally, one or more projections 62 are configured to be received within one or more grooves 61. In one embodiment, the projections 62 are configured to be received within the grooves when the locking arrangement 50 is in a locked position. In alternative embodiments, the projections 62 may be configured to be received within the grooves 61 when in an unlocked position. Some embodiments are described below. In one embodiment, at least one projection 62 is compressed radially inwards when the locking element 51 is in an unlocked position and expands radially outward into at least one groove 61 when in the locking element 51 is in a locked position. The locking aperture 52 may or may not extend from the upper surface 12 of the plate 10 all the way to the bone-contacting surface 11.

The locking element 51 can include one projection 62 configured to be received within at least one groove 61 or a plurality of projections 62, typically between two and four, preferably three or four projections configured to be received within a plurality of grooves. Typically, the number of grooves 61 is the same as, or greater, than the number of projections 62.

Figure 19:
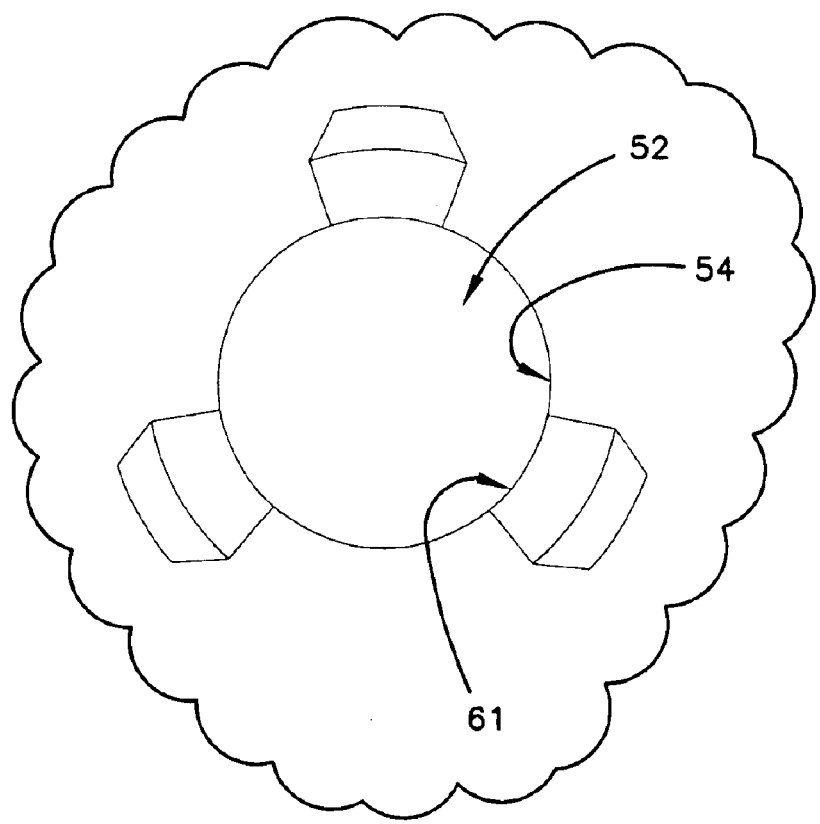
FIG. 19 is an enlarged bottom view of a grooved locking aperture with a locking element in a locked position.

In one embodiment, one or more projections 62 of the locking element 51 extend along the longitudinal axis (a'—a') of the locking element 51. In one embodiment, one or more projections 62 include distinct "legs" 63 that extend from the locking cover 53. The term "legs" 63 is meant to distinguish this embodiment from others in which one or more projections 62 protrude, similar to a ridge or bump, from the shaft of the locking element 51. In a preferred embodiment, the locking element 51 includes three legs 63 that extend from the base of the locking cover 53 (FIG. 18). The locking aperture 52 may include grooves 61 that extend in a direction configured to receive the projections 62 when the locking element 51 is in a locked position (FIGS. 19 and 21). The grooves 61 may or may not extend all the way from the upper surface 12 of the plate 10 to the bone-contacting surface 11.

Figure 25:
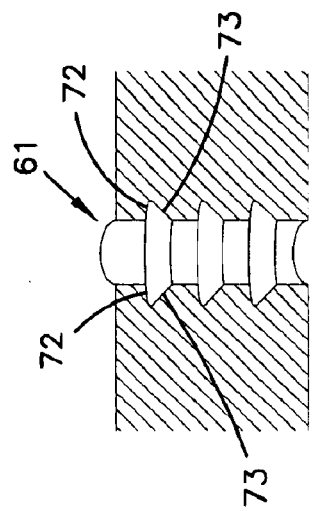
FIG. 25 is a cross sectional view of a locking aperture with an alternative groove pattern.

Other embodiments for a "snap-fit" locking arrangement are envisioned. For example, the locking element 51 may include a locking cover 53 and a shaft 57 that has one or more projections 62 that are oriented transverse to the longitudinal axis (a'—a') of the locking element 51. In this embodiment, the locking aperture 52 may have one or more grooves 61 that are configured to receive the projections 62 of the locking element 51 when the locking element 51 is in a locked position. For example, one or more grooves may extend "horizontally" within the locking aperture 52 (FIG. 25). As the locking element 51 is advance within the locking aperture 52, one or more projections 62 are compressed radially inward. Once the locking element 51 is advanced such that the projections 62 align with one or more grooves 62, one or more projections 62 expand radially outward, into the groove 62. The horizontal groove 62 has an upper 72 and a lower 73 surface. Typically the upper surface 72 is oriented in a direction substantially transverse or perpendicular to the longitudinal axis L—L of the locking aperture 52 to secure the projection 62 within the groove 61. The lower surface 73 may be ramped or angled with respect to the longitudinal axis L—L of the aperture 52, to facilitate advancement of the locking element 51 within the aperture 52.

Figure 24:
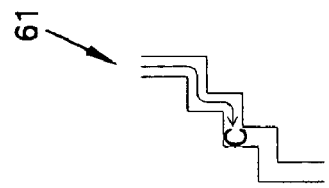
FIG. 24 is a schematic of an alternative groove pattern.
Figure 23:
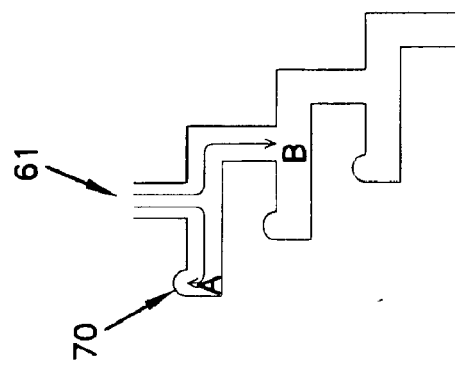
FIG. 23 is a schematic of a groove pattern.
Figure 26:
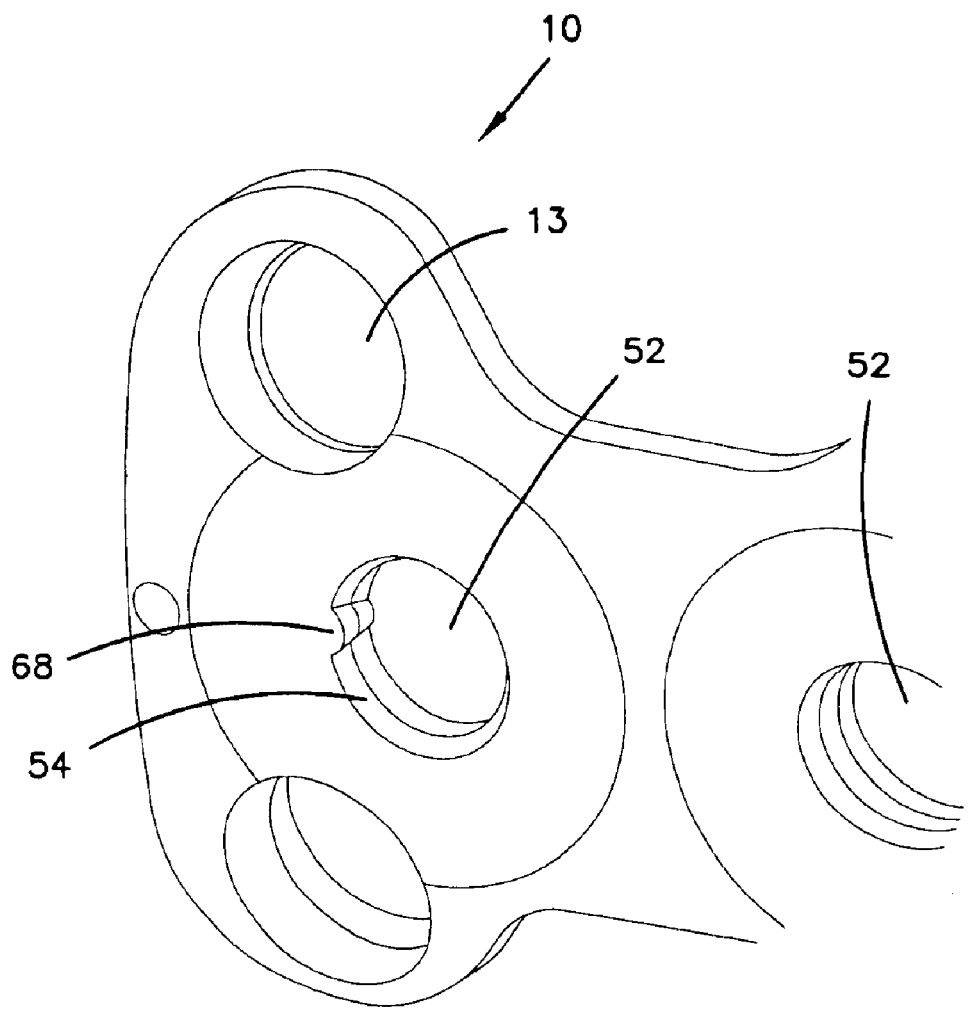
FIG. 26 is an enlarged view of an alternative embodiment of a locking aperture.

Other groove configurations are shown in FIGS. 23 and 24. A locking element 51 having one or more projections 62 configured to fit within a groove 61 having configuration shown in FIG. 23 can be used. In this embodiment, the one or more projections 62 "track" the groove 61 as the locking element 51 is advanced within the locking aperture (i.e., the projections 62 are present within the groove when the locking element is in both the locked and unlocked position). As the locking element 51 is advanced into the fastener-receiving aperture 13, the projections 62 "track" the grooves 61, and the locking element 51 is rotated generally in the direction of arrow "B". When the locking element 51 is positioned at a desired location, the locking element 51 can be rotated in the direction of arrow "A" until the projection 62 rests within the locking pocket 70. If it is desirable to advance the locking element 51 further within the locking aperture 52, the locking element 51 can be rotated in the direction of arrow "B".

Yet another groove configuration is shown in FIG. 24. In this configuration, one or more projections 62 on the shaft 57 of the locking element 51 are configured to fit within a groove 61 having the configuration shown. The locking element 51 is rotated in the direction of arrow "C" to rotatably advance the locking element 51 into the locking aperture 52.

Still other groove configurations are envisioned and fall within the scope of the invention.

In one embodiment, the locking element 51 may also include one or more anchors 64 configured to secure the locking element 51 within the locking aperture 52. In one embodiment, the anchor 64 is a flange that extends radially outward from shaft 57 of the locking element 51, most typically from the tip 65 of the shaft 57. In one embodiment, the anchor 64 is configured to contact the bone-contacting surface 11 of the plate 10. In an alternative embodiment, the locking aperture 52 includes a second countersink 67 in the bone-contacting surface 11 of the plate 10. The anchor 64 of the locking element 51 is configured to be received within the second countersink 67.

B. Deformable Member

In another embodiment, the locking arrangement 51 includes one or more locking elements 51, one or more locking apertures 52, and a deformable member 68 disposed between the surface 54 of the locking aperture 52 and the surface 69 of the shaft 57 of the locking element 51. According to this embodiment, the deformable member 68 deforms when the locking element 51 is secured within the locking aperture 52. The deformation of the deformable member 68 helps secure the locking element 51 within the locking aperture 52.

A variety of locking elements 51 can be used in connection with the deformable member, many of which are described above. In one embodiment, the locking element 51 is rotatably mounted within the locking aperture 52. In an alternative embodiment, the locking element 51 is secured within the locking aperture 52 by frictional engagement or a snap engagement.

The deformable member 68 can be any suitable size and shape. In one embodiment, the deformable member 68 is in the shape of a cylinder and has a length about its longitudinal axis that is less than or equal to the length of a longitudinal axis of locking aperture 52. Typically, the deformable member 68 is smaller than the aperture 52. More typically, the deformable member is at least about 50% smaller than the aperture. The deformable member 68 can be mounted to the inner surface 54 of the locking aperture or to the shaft 57 of the locking element 51. Preferably, the deformable member 68 is constructed from a biocompatible plastic material. In one embodiment, the deformable member 68 is constructed from ultra high molecular weight polyethylene (UHMWPE).

C. Timing

In another embodiment, the locking arrangement 50 includes one or more threaded rotatable locking elements 51 having a predetermined locked position and/or a predetermined unlocked position and one or more locking apertures 52 with an inner surface 54 that includes threads 55. The threads of the locking element 51 are configured to mate with the threads 55 of the locking aperture 52 such that the base has a predetermined initial and final position. Various timing arrangements are known.

D. Timing Combined with Deformable Member

In another embodiment, the locking arrangement 51 includes a timing mechanism, such as the one described above, in combination with a deformable member 68. In this embodiment, the timing mechanism determines at least a final position of the locking element 51, and may also determine an initial position, if desired. The deformable member 68 prevents the locking arrangement 51 from "unwinding" once the final position is obtained.

According to this embodiment, a deformable member 68 is disposed between the inner surface 54 of the locking aperture 52 and the surface 69 of the shaft 57 of the locking screw 56. The threads of the locking element 51 are configured to mate with the threads 55 of the locking aperture 52 such that the base has a predetermined initial and final position. As the locking element 51 is rotated, the deformable member 68 becomes deformed, making it more difficult to "unwind" the locking member.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

What is claimed is:

1. A bone fixation device, comprising:
   a plate, comprising:
      a bone-contacting surface;
      an upper surface opposite the bone-contacting surface; and
      a fastener-receiving aperture extending through the plate from the upper surface to the bone-contacting surface, wherein the fastener-receiving aperture comprises a frustoconcial inner surface; and
   a fastener having a head that has bulbous outer surface, which contacts the frustoconical inner surface of the fastener-receiving aperture when the fastener is received within the fastener-receiving aperture.

2. The bone fixation device according to claim 1, wherein the bulbous outer surface comprises a spherical outer surface.

3. The bone fixation device according to claim 1, wherein the fastener comprises a screw.

4. The bone fixation device according to claim 1, wherein the bulbous outer surface of the head forms a ring of contact with the frustoconcial inner surface of the fastener-receiving aperture during fixation of a bone with the device.

5. The bone fixation device according to claim 1, wherein the frustoconical inner surface of the fastener-receiving aperture includes a major opening proximate the upper of the plate and a minor opening proximate the bone-contacting surface.

6. The bone fixation device according to claim 5, wherein the screw comprises:
   the head having a diameter greater than a diameter of the minor opening; and
   an upper shaft having a diameter that matches the diameter of the minor opening.

7. The bone fixation device according to claim 6, wherein the upper shaft of the screw comprises:
   a major component proximate the head of the screw, wherein the major component has a diameter that matches the diameter of the minor opening; and
   a minor component distal to the head wherein the minor component has a diameter that is less than the diameter of the minor opening.

8. The bone fixation device according to claim 1, wherein the fastener-receiving aperture comprises a major opening proximate the upper surface and a minor opening proximate the bone-contacting surface, wherein the major opening includes the frustoconical inner surface.

9. The bone fixation device according to claim 8, wherein the minor opening has a cylindrical inner surface.

10. The bone fixation device according to claim 8, wherein the screw comprises:
   the head having a diameter that is greater than a diameter of the minor opening; and
   an upper shaft having a diameter that is less than the diameter of the minor opening.

11. The bone fixation device according to claim 1, further comprising a locking arrangement configured to secure the fastener within the fastener-receiving aperture.

12. The bone fixation device according to claim 11, wherein the locking arrangement comprises:
   a locking element; and
   a locking aperture.

13. The bone fixation device according to claim 12, wherein the locking element is rotatable within the locking aperture.

14. The bone fixation device according to claim 12, wherein the locking element comprises a locking cover and a shaft.

15. The bone fixation device according to claim 14, wherein the locking element has an unlocked position that permits insertion of a screw into the fastener-receiving aperture and a locked position in which the locking cover at least partially obstructs the fastener-receiving aperture.

16. The bone fixation device according to claim 14, wherein the locking element comprises a removable screw having a threaded shaft, wherein the threads are configured to mate with a threaded interior of the locking aperture.

17. The bone fixation device according to claim 12, wherein the locking element comprises a cap having circumferential threads configured to mate with a threaded inner surface of the locking aperture.

18. The bone fixation device according to claim 12, wherein:
   the locking aperture comprises an inner surface having a groove; and
   the locking element comprises:
      a locking cover configured to secure the screw within the fastener-receiving aperture; and a shaft comprising a projection configured to be received within the groove.

19. The bone fixation device according to claim 18, wherein the locking arrangement has a locked and an unlocked position.

20. The bone fixation device according to claim 18, wherein the projection is configured to be received within the groove when the locking element is in a locked position.

21. The bone fixation device according to claim 18, wherein the shaft of the locking element comprises a plurality of projections.

22. The bone fixation device according to claim 21, wherein the locking aperture comprises a plurality of grooves.

23. The bone fixation device according to claim 18, wherein the locking aperture comprises a groove.

24. The bone fixation device according to claim 18, wherein the locking element further comprises an anchor configured to secure the locking element within the locking aperture.

25. The bone fixation device according to claim 24, wherein the anchor comprises a flange that extends radially outward from the shaft of the locking element.

26. The bone fixation device according to claim 18, wherein the projection is compressed radially inwards when the locking element is in an unlocked position and expands radially outward in the groove when in a locked position.

27. The bone fixation device according to claim 11, wherein the locking arrangement comprises:
a locking aperture within the upper surface of the plate, the locking aperture having a threaded inner surface; and
a locking element, comprising:
a locking cover configured to contact the upper surface of the plate; and
a threaded shaft rotatably mounted within the locking aperture wherein the threads of the shaft are configured to mate with the threads of the locking aperture such that the locking element has a predetermined initial and final position;
a deformable member disposed between the locking element and the inner surface of the locking aperture.

28. The bone fixation device according to claim 27, wherein the locking arrangement has predetermined locked and unlocked positions.

29. The bone fixation device according to claim 1, further comprising a plurality of fasteners, a plurality of fastener-receiving apertures and a plurality of locking arrangements each configured to secure one of the fasteners within one or more of the fastener-receiving apertures.

30. The bone fixation device according to claim 1, wherein the plate is an anterior cervical plate.

31. The bone fixation device according to claim 1, wherein the plate comprises a plurality of connectable plates.

32. The bone fixation device according to claim 1, wherein the plate is concave along a longitudinal axis and a transverse axis.

33. The bone fixation device according to claim 1, further comprising a locking arrangement rotatably mounted to the plate, the locking arrangement comprising:
a locking aperture within the upper surface of the plate, the locking aperture having an inner surface; and
a locking element, comprising:
a locking cover configured to secure the screws in the fastener-receiving aperture; and
a shaft rotatably mounted within the locking aperture;
a deformable member disposed between the shaft of the locking element and the inner surface of the locking aperture.

34. The bone fixation device according to claim 33, wherein the deformable member comprises a deformable cylinder.

35. The bone fixation device according to claim 33, wherein the deformable member is constructed from ultra high molecular weight polyethylene (UHMWPE).

36. A bone fixation device, comprising:
a plate comprising:
a bone-contacting surface;
an upper surface opposite the bone-contacting surface; and
a fastener-receiving aperture extending through the plate from the upper surface to the bone-contacting surface, wherein the fastener-receiving aperture comprises:
a major opening proximate the upper surface, wherein the major opening comprises a frustoconical inner surface; and
a minor opening proximate the bone-contacting surface; and
a screw having a head that has bulbous outer surface positioned adjacent the frustoconical inner surface of the fastener-receiving aperture during fixation of a bone with the device.

37. The bone fixation device according to claim 36, wherein the minor opening comprises a cylindrical inner surface.

38. A bone fixation device, comprising:
one or more plates, each comprising:
a bone-contacting surface;
an upper surface opposite the bone-contacting surface; and
one or more fastener-receiving apertures extending through the plate from the upper surface to the bone-contacting surface, wherein at least one fastener-receiving aperture comprises:
a major opening proximate the upper surface, wherein the major opening comprises a frustoconical inner surface; and
a minor opening proximate the bone-contacting surface, wherein the minor opening comprises a cylindrical inner surface; and
one or more screws including a head having an arcuate outer surface with a diameter that is greater than a diameter of the minor opening, wherein the arcuate outer surface of the screw head is positioned adjacent the frustoconical inner surface of the fastener-receiving aperture during fixation of a bone with the device, an upper shaft having a diameter that is less than the diameter of the minor opening.

39. A kit comprising:
a plate, comprising:
a bone-contacting surface;
an upper surface opposite the bone-contacting surface; and
a fastener-receiving aperture extending through the plate from the upper surface to the bone-contacting surface, wherein the fastener-receiving aperture comprises a frustoconical inner surface; and
a fastener having a head that has bulbous outer surface, wherein the fastener is configured to be received within the fastener-receiving aperture; and
a locking arrangement configured to secure the one or more fastener in the one or more fastener-receiving apertures.

40. The kit according to claim 39, wherein the fastener comprises a screw.

41. A bone fixation device, comprising:
- a bone plate having a bone-contacting surface and an opposite upper surface, the bone plate defining an aperture that extends through the plate from the upper surface to the bone-contacting surface, the aperture including a first contact surface having a first cross-sectional configuration; and
- a fastener having a fastener head, the fastener head including a second contact surface having a second, non-corresponding, cross-sectional configuration to that of the first cross-sectional configuration of the aperture;
- wherein the second contact surface of the fastener head contacts the first contact surface of the aperture when the fastener head is positioned within the aperture of the bone plate.

42. The device of claim 41, wherein the first contact surface of the aperture has a frustoconical configuration.

43. The device of claim 41, wherein the second contact surface of the fastener head has an arcuate configuration.

44. The device of claim 41, wherein a ring-shaped line of contact is formed between the first contact surface of the aperture and the second contact surface of the fastener head.

45. A bone fixation device, comprising:
- a bone plate having a bone-contacting surface and an opposite upper surface, the bone plate defining a plurality of fastener-receiving apertures extending through the plate from the upper surface to the bone-contacting surface, the fastener-receiving apertures having a first contact surface; and
- a plurality of fasteners each having a head that is received within one of the fastener-receiving apertures, the heads of the fasteners having a second contact surface;
- wherein the first and second contact surfaces have non-corresponding geometries such that a ring of contact is formed between the first contact surface of the plate and the second contact surface of the fasteners.

* * * * *

UNITED STATES PATENT AND TRADEMARK OFFICE
CERTIFICATE OF CORRECTION

PATENT NO. : 6,890,335 B2
DATED : May 10, 2005
INVENTOR(S) : John J. Grabowski et al.

It is certified that error appears in the above-identified patent and that said Letters Patent is hereby corrected as shown below:

Column 11,
Line 55, "frustroconcial" should read -- frustroconical --.
Line 56, before "bulbous" insert -- a --.

Column 12,
Line 3, after "upper" and before "of" insert -- surface --.

Column 13,
Line 65, delete "screws" and insert therefor -- screw --.

Column 14,
Line 62, before "bulbous" insert -- a --.
Line 66, delete "fastener" and insert therefor -- fasteners --.

Signed and Sealed this

Eleventh Day of October, 2005

JON W. DUDAS
*Director of the United States Patent and Trademark Office*